US010449232B2

(12) United States Patent
Miossec et al.

(10) Patent No.: US 10,449,232 B2
(45) Date of Patent: Oct. 22, 2019

(54) PUMA PROTEIN EXPRESSION VECTOR AND USE THEREOF IN GENE THERAPY

(71) Applicants: HOSPICES CIVILS DE LYON, Lyons (FR); THE REGENTS OF THE UNIVERSITY OF CALIFORNIA, Oakland, CA (US); UNIVERSITE CLAUDE BERNARD-LYON 1, Villeurbanne (FR); INSTITUT D'ENSEIGNEMENT SUPERIEUR ET DE RECHERCHE EN ALIMENTATION, SANTE ANIMALE, SCIENCES AGRONOMIQUES ET DE L'ENVIRONNEMENT, Marcy l'etoile (FR); INSTITUT NATIONAL DE LA SANTE ET DE LA RECHERCHE MEDICALE (INSERM), Paris (FR)

(72) Inventors: Pierre Miossec, Bron (FR); Saw-See Hong, Lyons (FR); Gary Firestein, Del Mar, CA (US)

(73) Assignees: Hospices Civils de Lyon, Lyons (FR); The Regents of the University of California, Oakland, CA (US); Universite Claude-Bernard-Lyon 1, Villeurbanne (FR); Institut D'Enseignement Superieur et de Recherche en Alimentation, Sante Animale, Sciences Argonomiques et de l'Environnement, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 15/027,375

(22) PCT Filed: Oct. 7, 2014

(86) PCT No.: PCT/IB2014/065118
§ 371 (c)(1),
(2) Date: Apr. 5, 2016

(87) PCT Pub. No.: WO2015/052651
PCT Pub. Date: Apr. 16, 2015

(65) Prior Publication Data
US 2016/0243194 A1 Aug. 25, 2016

(30) Foreign Application Priority Data
Oct. 8, 2013 (FR) .................................... 13 59751

(51) Int. Cl.
*A61K 38/17* (2006.01)
*A61K 35/76* (2015.01)
*A61K 35/761* (2015.01)
*C12N 7/00* (2006.01)
*C12N 15/86* (2006.01)

(52) U.S. Cl.
CPC .......... *A61K 38/1761* (2013.01); *A61K 35/76* (2013.01); *A61K 35/761* (2013.01); *C12N 7/00* (2013.01); *C12N 15/86* (2013.01); *C12N 2710/00022* (2013.01); *C12N 2710/10322* (2013.01); *C12N 2710/10333* (2013.01); *C12N 2710/10343* (2013.01); *C12N 2710/14033* (2013.01); *C12N 2710/14143* (2013.01); *C12N 2710/14145* (2013.01); *C12N 2800/40* (2013.01); *C12N 2810/855* (2013.01)

(58) Field of Classification Search
None
See application file for complete search history.

(56) References Cited

U.S. PATENT DOCUMENTS

2007/0065421 A1* 3/2007 Firestein ................ A61K 38/17
424/93.21

FOREIGN PATENT DOCUMENTS

WO  2007/035494 A2  3/2007
WO  2011/042769 A1  4/2011

OTHER PUBLICATIONS

Toh et al. Enhancement of Adenovirus-Mediated Gene Delivery to Rheumatoid Arthritis Synoviocytes and Synovium by Fiber Modifications: Role of Arginine-Glycine-Aspartic Acid (RGD)- and Non-RGD-Binding Integrins. The Journal of Immunology, 2005. 175:7687-7698.*
International Search Report issued in corresponding International Patent Application No. PCT/IB2014/065118 dated Jan. 26, 2015.
Toh et al., "Enhancement of Adenovirus-Mediated Gene Delivery to Rheumatoid Arthritis Synoviocytes and Synovium by Fiber Modifications: Role of Arginine-Glycine-Aspartic Acid (RGD)- and Non-RGD-Binding Integrins," Journal of Immunology, 175: 7687-7698 (2005).
Kammouni et al., "Regulation of Apoptosis in Fibroblast-like Synoviocytes by the Hypoxia-Induced Bcl-2 Family Member Bcl-2/Adenovirus E1B 19-kd Protein-Interacting Protein 3," Arthritis & Rheumatism, 56: 2854-2863 (2007).
Niedermeier et al., "Therapeutic opportunities in fibroblasts in inflammatory arthritis," Best Practice & Research Clinical Rheumatology, 24: 527-540 (2010).
Malemud, "Apoptosis Resistance in Rheumatoid Arthritis Synovial Tissue," Journal of Clinical & Cellular Immunology, 1: 1-13 (2011).

* cited by examiner

*Primary Examiner* — Christopher M Babic
*Assistant Examiner* — Kimberly A. Aron
(74) *Attorney, Agent, or Firm* — Morgan, Lewis & Bockius LLP

(57) ABSTRACT

The present invention relates to a viral vector for expression of the cell death-inducing PUMA protein, for use in gene therapy, for example for the treatment of rheumatoid arthritis. This vector consists in particular of a recombinant adenovirus expressing the gene encoding the PUMA protein and of a recombinant baculovirus containing a coxsackie-adenovirus receptor (CAR).

8 Claims, 10 Drawing Sheets

(a) BV$^{CAR}$ alone (b) HAdV5-PUMA alone
(10$^9$UFP)

(c) BV$^{CAR}$HAdV5-PUMA
(10$^7$ UFP)

(d) BV^CAR HAdV5-PUMA
    (10^9 UFP)

(e) Control heel
    of a healthy rat

PUMA PROTEIN EXPRESSION VECTOR AND USE THEREOF IN GENE THERAPY

The present invention relates to a viral vector for expression of the PUMA (p53 up-regulated modulator of apoptosis) protein, an inducer of cell death, for use of same in gene therapy, in particular for rheumatoid arthritis.

Rheumatoid arthritis (RA) is an autoimmune disease that causes chronic inflammation of the joints and surrounding tissue. The inflammation is maintained by cytokines produced by synovial macrophages and fibroblasts, such as tumor necrosis factor alpha (TNF-α) and interleukin 1 (IL-1), and by other cells such as T lymphocytes, such as interleukin 17 (IL-17). The proliferation of fibroblast-like synoviocytes (FLS), or B-type synoviocytes (hereinafter referred to as "synoviocytes"), contributes to the inflammatory process by accumulation of cells in the intima of the synovium (Firestein, *Arthritis Rheum.*, 39:1781-90, 1996). In fact, whereas in a healthy joint, the synoviocytes participate in biochemical equilibrium by secreting different proteins and cytokines, in an arthritic joint, they undergo modifications resulting in their proliferation, the release of anti-apoptotic proteins, proinflammatory cytokines and proteolytic enzymes, such as collagenases.

The current treatments for rheumatoid arthritis involve biotherapy, in particular anti-TNF biotherapy. However, 40% of patients do not respond to the treatment or respond by a transient therapeutic effect. It has been suggested that local treatments involving the induction of apoptosis of synoviocytes may be an effective treatment for rheumatoid arthritis (Firestein, *Nature*, 423: 356-61, 2003).

In this way, a plurality of genes coding for pro-apoptotic proteins have been evaluated as potential therapeutic gens, for example genes coding for the proteins Fas (Okamoto et al., *Gene Ther.*, 5:331-8, 1998), TRAIL (tumor necrosis factor-related apoptosis-inducing ligand) (Yao et al., *Arthr. Res. Ther.*, 8: IR16, 2006), and p53 (Yao et al., *Mol. Ther.*, 3(6): 901-10, 2001).

Among these pro-apoptotic proteins, in particular the "BH3-only" proteins of the Bcl-2 family will be cited. The PCT application WO 2007/035494 proposes the use of these proteins for inducing apoptosis in synoviocytes. Preliminary results have demonstrated that in vitro transduction of synoviocytes with a plasmid vector expressing the PUMA protein (PCT WO 2007/035494; Cha et al., *Arthritis & Rheumatism*, 54(2): 587-92, 2006; You et al., 2006, mentioned above) made it possible to induce apoptosis of the transduced cells. Other experiments of the same type have demonstrated that the "BH3-only" protein BNIP3 had the same pro-apoptotic properties, but complementary tests performed in the presence of proinflammatory cytokines, such as TNF-α and IL-1β, have demonstrated that this pro-apoptotic effect was partially inhibited by said proinflammatory cytokines, which are abundant in joints affected by rheumatoid arthritis (Kammouni et al., *Arthritis & Rheum.*, 56(9): 2854-63, 2007).

The inventors studied in greater depth the effects of the PUMA protein on apoptosis of synoviocytes in an inflammatory context, in order to determine whether the use of this protein in vivo in the treatment of rheumatoid arthritis could actually be envisaged. To this end, they first, in order to obtain an effective in vivo expression, sought an alternative to the plasmid vectors used in the prior art.

Recombinant adenoviruses are among the vectors most commonly used in vivo, for the expression of genes for a therapeutic purpose. However, certain cells, including synoviocytes, are resistant to transduction by an adenoviral vector. No vector enabling the effective transduction of synoviocytes for delivering the gene coding for the PUMA protein to these cells has been described at present.

A number of studies have demonstrated that the refractory condition of certain cells to adenovirus transduction was tied to the absence of the CAR (coxsackie-adenovirus receptor) glycoprotein at the surface of the primary human cells or continuous cell lines (Gaden et al., *Am. J. Respir. Cell Mol. Biol.*, 27: 628-40, 2002), or to the low accessibility of CAR at the apical pole of the human epithelium (Granio et al., *Hum. Gene Ther.*, 21: 1-19, 2010; Walters et al., *J. Biol. Chem.*, 274: 10219-226, 1999). CAR is the cell receptor with high affinity for the adenoviral vector type 5, HAdV5 (Bergelson et al., Science, 275: 1320-23, 1997; Tomko et al., *Proc. Natl Acad. Sci. USA*, 94: 3352-6, 1997), as well as for other adenovirus serotypes (Arnberg, *Rev. Med. Virol.*, 19: 165-78, 2009). HAdV5 is the model adenovirus serotype, most commonly used for the construction of therapeutic vectors. Different strategies have been developed in order to redirect HAdV5 vectors to receptors other than CAR (Arnberg, 2009, mentioned above; Russell, *J. Gen. Virol.*, 90: 1-20, 2009). Most of these strategies have involved modifications of the adenovirus viral particle fiber (Arnberg, 2009, mentioned above; Corjon et al., *Mol. Ther.*, 16, 1813-24, 2008; Henning et al., *Gene Ther.* 12: 211-24, 2005; Henning et al., *Hum. Gene Ther.*, 13: 1427-39, 2002; Hong et al., *Mol. Ther.*, 7: 692-9, 2003; Law et al., *Mol. Ther.*, 12: 599-609, 2005; Magnusson et al., *Cancer Gene Ther.*, 14: 468-79, 2007; Magnusson et al., *J. Virol.*, 75: 7280-9, 2001; Magnusson et al., *J. Gene Med.*, 4: 356-70, 2002; Russell, 2009, mentioned above), the fiber being the capsid protein involved in the recognition of cell surface receptors by the adenovirus. However, certain genetic modifications of the gene of the adenovirus fiber have been identified as being detrimental to the viability or growth rate of resulting vectors (Henning et al., *J. Gen. Virol.*, 87: 3151-60, 2006; Magnusson et al., 2002, mentioned above). In other cases, the modifications of the vector have only slightly improved transduction. For example, genetically modified HAdV5 vectors, designed to target the integrin molecules at the surface of the synoviocytes, have led only to a modest improvement in the efficacy of transduction of said cells in vitro and ex vivo (Toh et al., *J. Immunol.*, 175(11): 7687-98, 2005).

Other strategies proposed have involved genetic and chemical modifications of HAdV5 (Kreppel et al., *Mol. Ther.*, 12: 107-117, 2005), or the coating of the viral capsid by a peptide or protein ligand used as a bifunctional adaptor, both for the virus and for the specific cell surface molecule (Hong et al., *Hum. Gene Ther.*, 10: 2577-86, 1999; Dreier et al., *J. Mol. Biol.* 405: 410-26, 2011).

Recently, it has been reported that the incorporation of the human CAR glycoprotein (GenBank NP_001329) in the envelope of a baculovirus produced a recombinant baculovirus, called $BV^{CAR}$ capable of forming, with HAdV5, a stable complex, and significantly increasing the transduction efficacy by HAdV5 of cells resistant to said transduction (PCT application WO 2011/042769; Granio et al., *J. of Virology*, 83(12): 6048-66, 2009).

The inventors tested whether the use of a recombinant baculovirus $BV^{CAR}$ could enable an increase in the efficacy of transduction of synoviocytes by an adenoviral vector carrying the gene coding for the PUMA protein. They observed that the HAdV5-$BV^{CAR}$ virus thus formed made it possible to very effectively transduce primary synoviocytes, and to induce their apoptosis. Moreover, the inventors observed that, contrary to what had been observed by Kammouni et al. with the "BH3-only" protein BNIP3, the presence of proinflammatory cytokines did not inhibit the pro-apoptotic effect of PUMA in the synoviocytes, but, by contrast, surprisingly, said cytokines induced an increase in the pro-apoptotic effect of PUMA, which is particularly beneficial in an inflammatory context.

The inventors also tested the therapeutic effect of the BV$^{CAR}$HAdV5-PUMA complex in the adjuvant-induced arthritis (AIA) model in the rat. They observed that the intra-articular injection of the BV$^{CAR}$HAdV5-PUMA complex in arthritic rats produced a significant dose-dependent clinical, functional and anatomical improvement in the joints treated. The inventors in particular demonstrated that, unlike the conventional vectors derived from HAdV5, which have a proinflammatory activity, BV$^{CAR}$HAdV5-PUMA has a global joint anti-inflammatory action. This joint anti-inflammatory action is significant, by comparison with the discrete reduction observed with the HAdV5-PUMA vector. Moreover, the significant joint anti-inflammatory activity of BV$^{CAR}$HAdV5-PUMA is detected at doses 10 times lower (in terms of number of viral particles of the HAdV5-PUMA active vector) than those used with the HAdV5-PUMA. These results demonstrate the therapeutic potential of the BV$^{CAR}$HAdV5-PUMA complex in the local treatment of joint pathologies.

This invention therefore relates to a complex consisting of (a) a recombinant adenovirus expressing the gene coding for the PUMA protein under the control of a functional promoter in a mammal cell, and (b) a recombinant baculovirus containing a mammal coxsackie-adenovirus receptor (CAR) inserted into its envelope, for use as a drug inducing apoptosis of synoviocytes for the local treatment of a joint disease associated with synoviocyte apoptosis failure.

As explained above, the complex according to the invention induces apoptosis of synoviocytes including in the presence of proinflammatory cytokines very effectively, which is especially beneficial in the local treatment of joint pathologies, in particular inflammatory pathologies.

Therefore, said joint disease may in particular be an inflammatory disease. The complex according to the invention may in particular be used for the treatment of joint inflammation due to rheumatoid arthritis or another type of inflammatory rheumatism, or occurring with arthritis flare-ups, chondrocalcinosis, gout, hemophilic arthropathy, loosening of prosthetic joints, or a synovial tumor as encountered in particular in the case of villonodular synovitis.

According to a preferred embodiment of the invention, said joint disease is rheumatoid polyarthritis.

The complex according to the invention is administered to an individual by a route suitable for local treatment of a joint disease and at doses sufficient for obtaining the desired therapeutic effect, which may easily be determined by a person skilled in the art.

The complex according to the invention will in particular be administered intra-articulately or peri-articularly, for example by injection or infiltration.

The adenovirus-BV$^{CAR}$ complexes capable of being used to express the PUMA protein in the context of this invention are those described in the PCT application WO 2011/042769. The PUMA protein is preferably the human protein. The sequence of the human PUMA protein was determined by Yu et al. (*Mol. Cell.*, 7(3): 673-82, 2001) and by Nakano et al. (*Mol. Cell.*; 7(3): 683-94-2001). The sequence of the cDNA and the human PUMA protein is recorded in GenBank, under number AF332558.

This invention will be easier to understand in view of the following description, which refers to non-limiting examples of embodiments of the invention, as well as to the appended drawings, wherein:

FIG. 1 shows the HAdV5-GFP-BV$^{CAR}$ complex observed in immune-electronic microscopy. The HAdV5-GFP vector appears to be an icosahedral particle 80 nm in diameter, associated with BV$^{CAR}$ in the form of a bar 300-350 nm in length. In FIG. 1a, the CAR molecules are identified by their immunoreactivity with an anti-CAR monoclonal antibody (CAR mAb) and a secondary antibody labeled with gold, appearing as a 20 nm colloid. In FIG. 1b, the envelope glycoproteins gp64 of the BV are in turn labeled with an anti-gp64 antibody (Gp64 mAb) and a secondary antibody labeled with gold.

Figure 4:
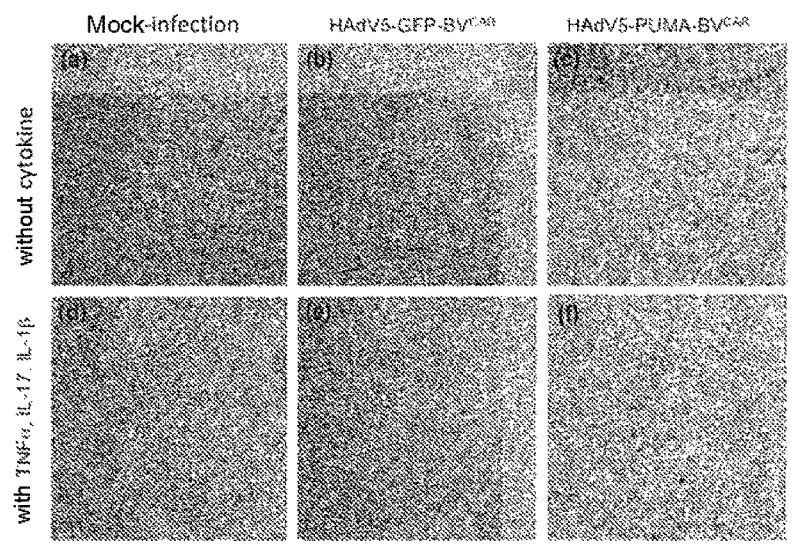

FIG. 4 shows the effect of the expression of the PUMA protein on human synoviocytes, observed with the microscope. The three photos of the top line (a, b, c) correspond to non-pretreated synoviocyte cultures and those of the bottom line (d, e, f) correspond to the synoviocytes pretreated with proinflammatory cytokines TNF-α, IL-17 and IL-1β. The left-hand column (a and d) shows the mock-infected cells, i.e. having been subjected to the infection protocol but in the absence of a vector (0 vp/cell), the middle column shows the cells infected with HAdV5-GFP-BV$^{CAR}$ (b and e) and the right-hand column shows the cells infected with HAdV5-PUMA-BV$^{CAR}$ complex (c and f).

Figure 5:
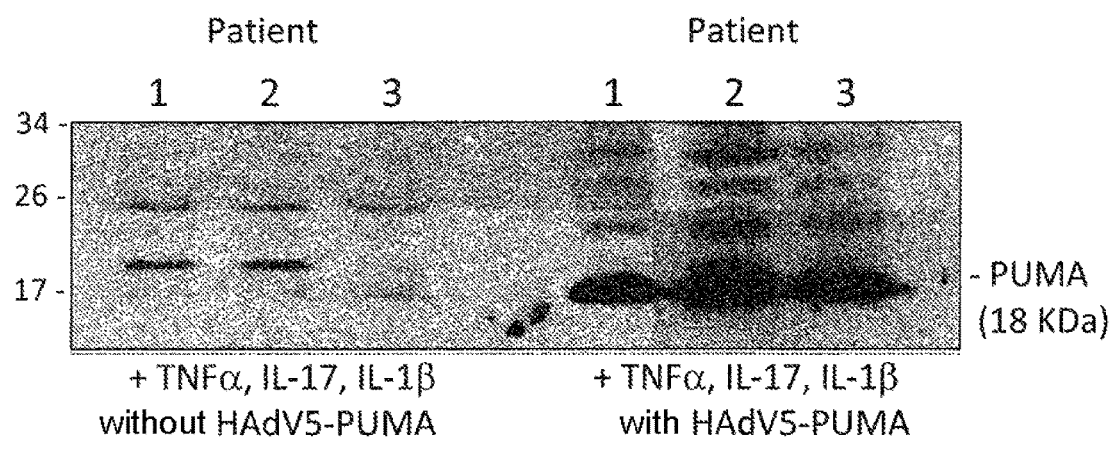

FIG. 5 shows the expression of the PUMA protein in multiple human synoviocyte samples (samples from patients 1, 2 and 3) pretreated with TNF-α, IL-17 and IL-1β, either non-infected (control samples, three left-hand columns), or infected by the viral complex HAdV5-PUMA-BV$^{CAR}$ (three right-hand columns). The PUMA protein (18 kDa) present in the cell lysates was identified by polyacrylamide-SDS gel electrophoresis followed by immunotransfer and identification by a specific anti-PUMA antibody.

Figure 6:
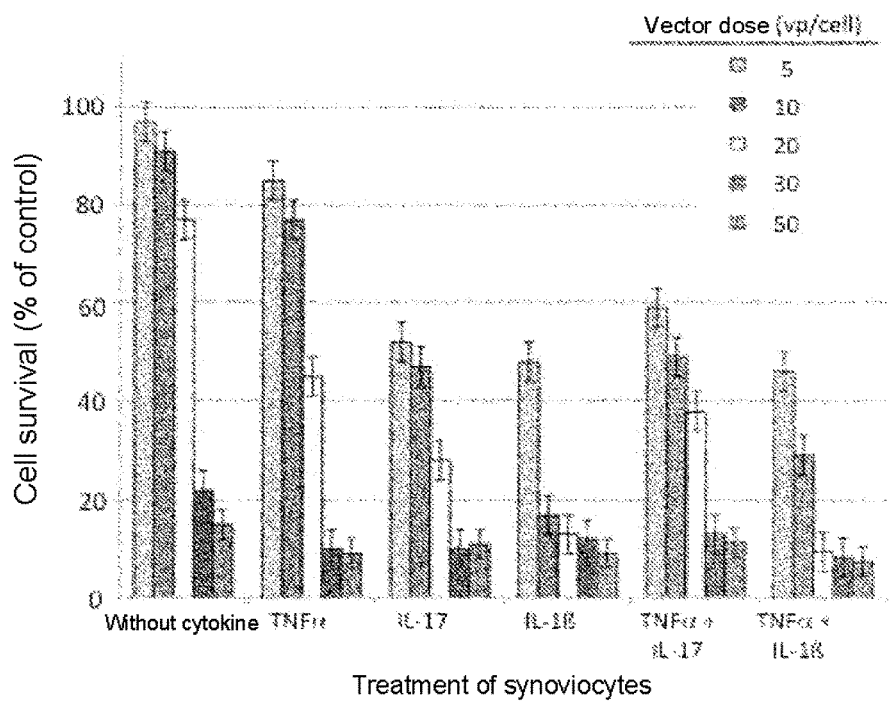

FIG. 6 shows the dependence on the vector dose of the PUMA-induced cell death. Human synoviocytes non-treated and treated with cytokines TNF-α, IL-17 and IL-1β, or in combination with TNF-α+IL-17 and TNF-α+IL-1β were infected with increasing doses of HAdV5-PUMA-BV$^{CAR}$. The cell death was evaluated by means of an MTT test, and the number of surviving cells was expressed as the percentage with respect to the control cells, mock-infected (0 vp/cell), the number of which defines the 100% value.

Figure 7:
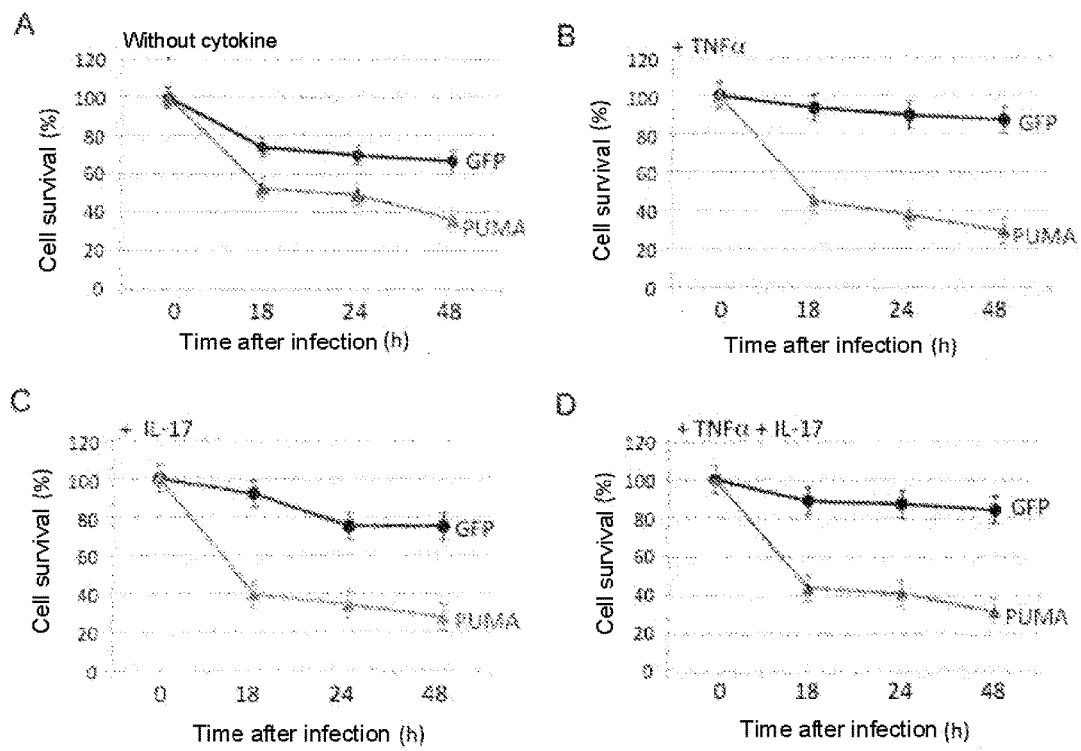

FIG. 7 shows the cell death kinetics due to the expression of PUMA. Synoviocytes non-treated (A) or treated with TNF-α (B), IL-17 (C) or a mixture of TNF-α and IL-17 (D), were infected at a constant vector dose of 20 vp/cell, and cell viability was monitored for 48 hours. HAdV5-GFP-BV$^{CAR}$ was used at the same vector dose as a control. Cell death was evaluated by an MTT test and the number of surviving cells is expressed as a percentage with respect to the number of control cells taken at time 0 of infection, to which the value 100% is assigned.

Figure 8:
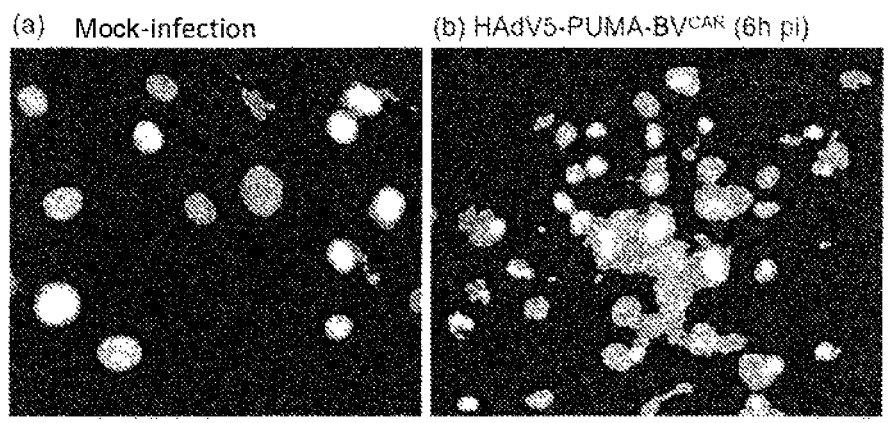

FIG. 8 shows the nuclear fragmentation of human synoviocytes infected with HAdV5-PUMA-BV$^{CAR}$ Fluorescence microscopy of mock-infected synoviocytes (0 vp/cell)

(a) and synoviocytes infected with HAdV5-PUMA-BV$^{CAR}$ at 50 vp/cell (b) and harvested 6 ours after infection (pi).

Figure 9:
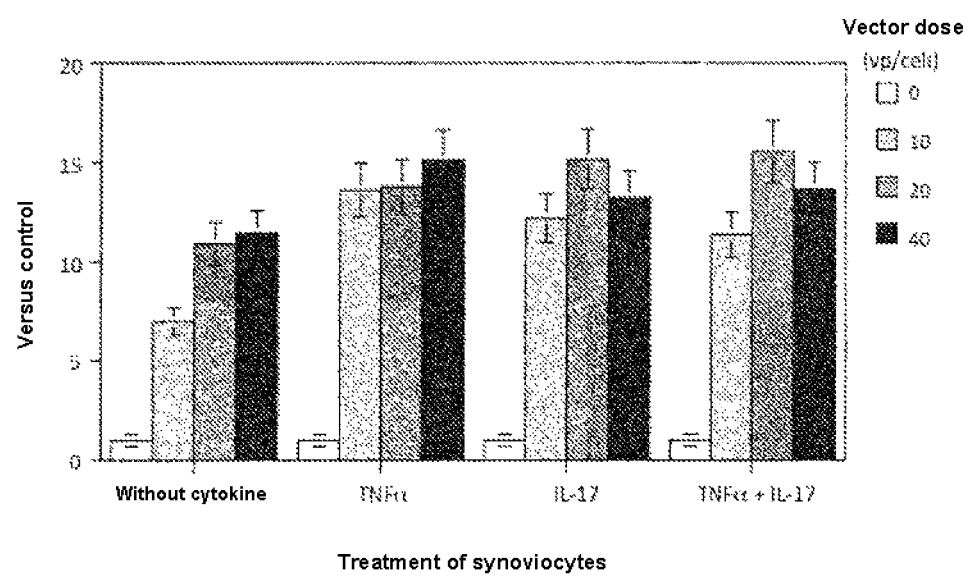

FIG. 9 shows the quantification of the cytoplasmic release of nucleosomes in human synoviocytes infected with HAdV5-PUMA-BV$^{CAR}$ Synoviocytes, treated or not with cytokines (TNF-α alone, IL-17 alone, or TNF-α and IL-17 in a mixture), were infected at increasing doses of HAdV5-PUMA-BV$^{CAR}$, and harvested 24 hours after infection. The fragmentation of the DNA and the release of the nucleosomes in the cytoplasm were determined by means of the immunologic detection of DNA fragments complexed with histones. The lysates of the mock-infected cells (0 vp/cell) served as a negative control for evaluating the basal level, i.e. the physiological nucleosome content in the cytoplasm. The results were expressed as multiples of the basal level, to which the value 1 was assigned.

Figure 10:
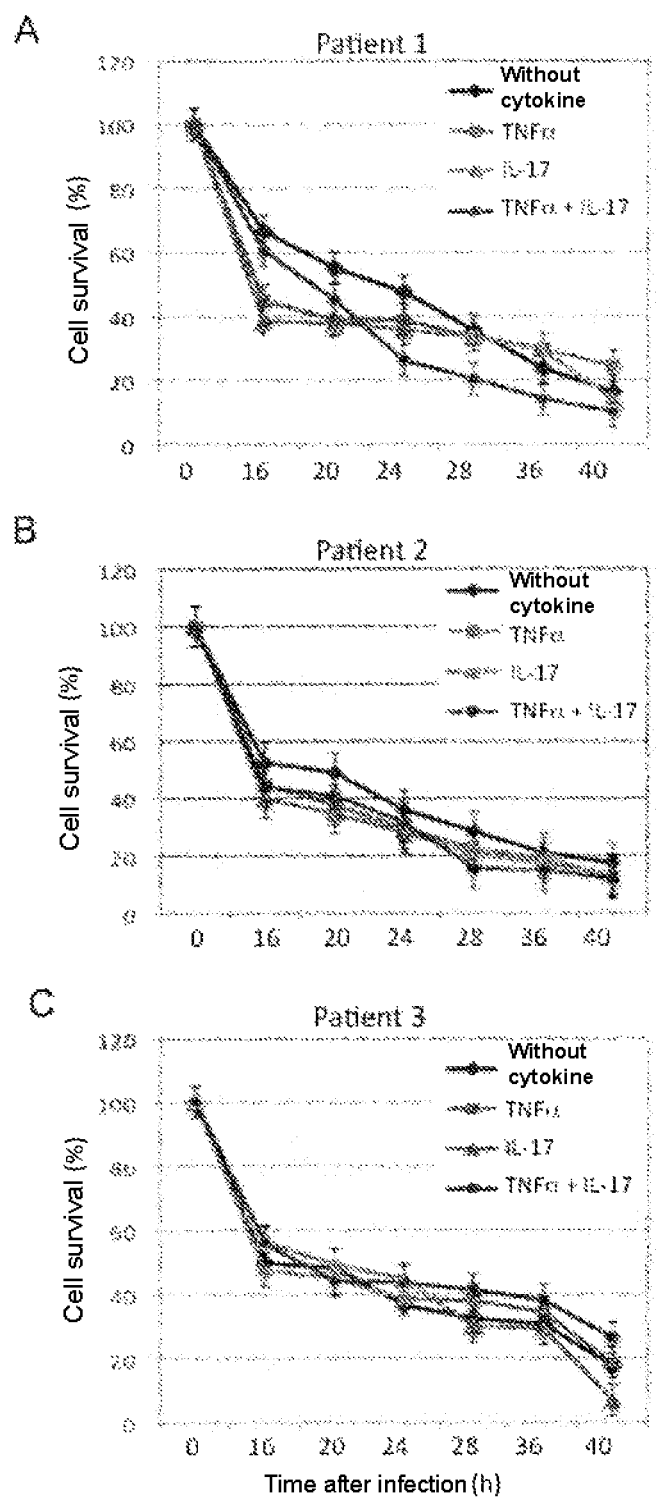

FIG. 10 shows the results of the infection of synoviocytes obtained from samples of 3 patients, by HAdV5-PUMA-BV$^{CAR}$ (A: patient 1; B: patient 2; C: patient 3). These synoviocytes, treated or not by cytokines (TNF-α alone, IL-17 alone, or TNF-α and IL-17 in a mixture), were infected with HAdV5-PUMA-BV$^{CAR}$ at a constant adenoviral vector dose of 50 vp/cell. The cell viability was monitored for 40 hours, by means of the MTT test. The number of surviving cells was expressed as the percentage of control cells, taken at time 0 of infection, to which the value 100% was assigned.

Figure 11:
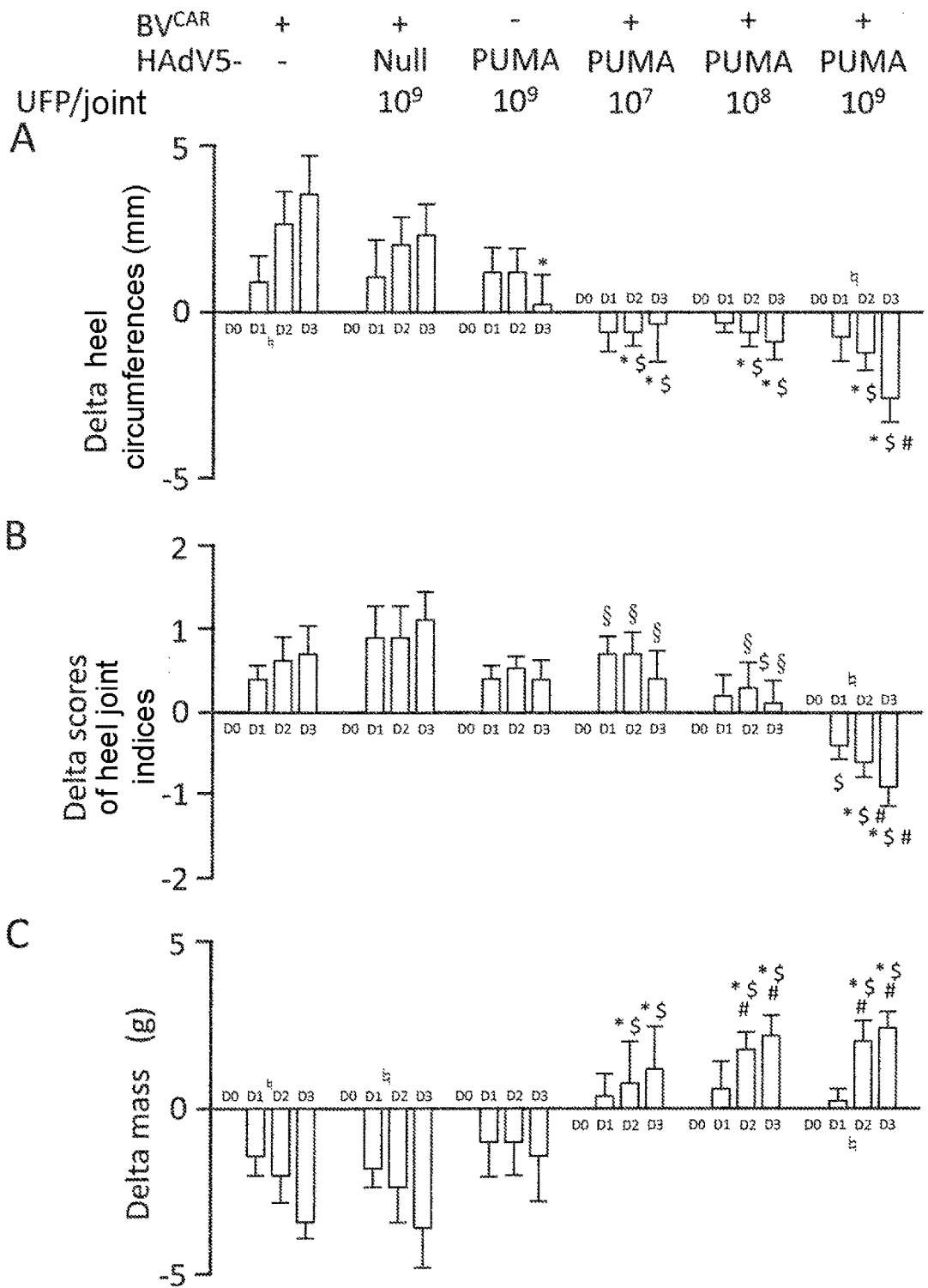

FIG. 11 shows the reduction in joint inflammation mediated by BV$^{CAR}$HAdV5-PUMA in the AIA model in the rat.

The rats develop arthritis 8-10 days after injection of adjuvant. Upon appearance of arthritis, 14 days after injection, the vectors (10 μL) were delivered to the joint of each heel. Thirty rats divided into 6 groups (5 rats per group) were used. The three control groups consisted of recombinant baculovirus alone (BV$^{CAR}$; 10$^5$ UFP per joint), the adenovirus vector carrying the PUMA gene alone (HAdV5-PUMA; 10$^9$ UFP per joint), and BV$^{CAR}$ (10$^5$ UFP per joint) in combination with the empty adenoviral vector (HAdV5-null; 10$^9$ UFP per joint). The three therapeutic groups consisted of the association of BV$^{CAR}$ (10$^5$ UFP per joint) with HAdV5-PUMA at 3 concentrations (10$^7$, 10$^8$, and 10$^9$ per joint, respectively). The values represented in the bar graph are averages ±SEM. The differences (Delta) in the biological parameters were defined by the values obtained on the day of follow-up minus the values obtained on the day of the intra-articular injection. (A), Differences in heel circumferences. The values of the heel circumferences were obtained by measuring the heel diameter with a perpendicular sliding caliper, by means of a geometric formula. (B) Differences in the heel joint index scores. (C), Differences in the body masses of the rats. Abbreviations: D, day after intra-articular injection of the vector; *$P<0.05$ versus BV$^{CAR}$ alone; $, $P<0.05$ versus BV$^{CAR}$HAdV5-null; #, $P<0.05$ versus HAdV5-PUMA alone; §, $P<0.05$ versus BV$^{CAR}$HAdV5-PUMA (10$^9$ UFP per joint); ⁞ $P<0.05$ by the one-way ANOVA test.

Figure 12:
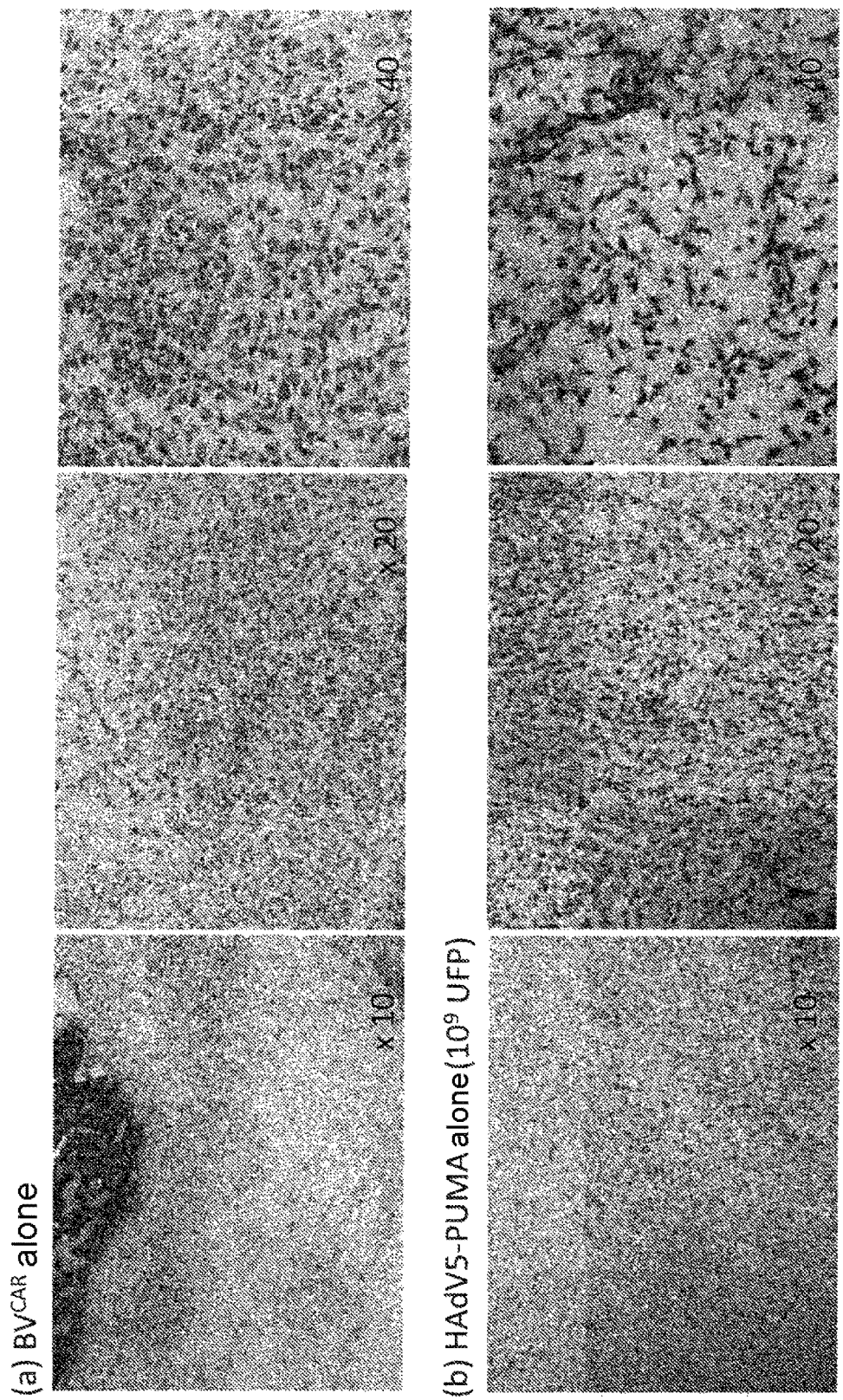
Figure 12:
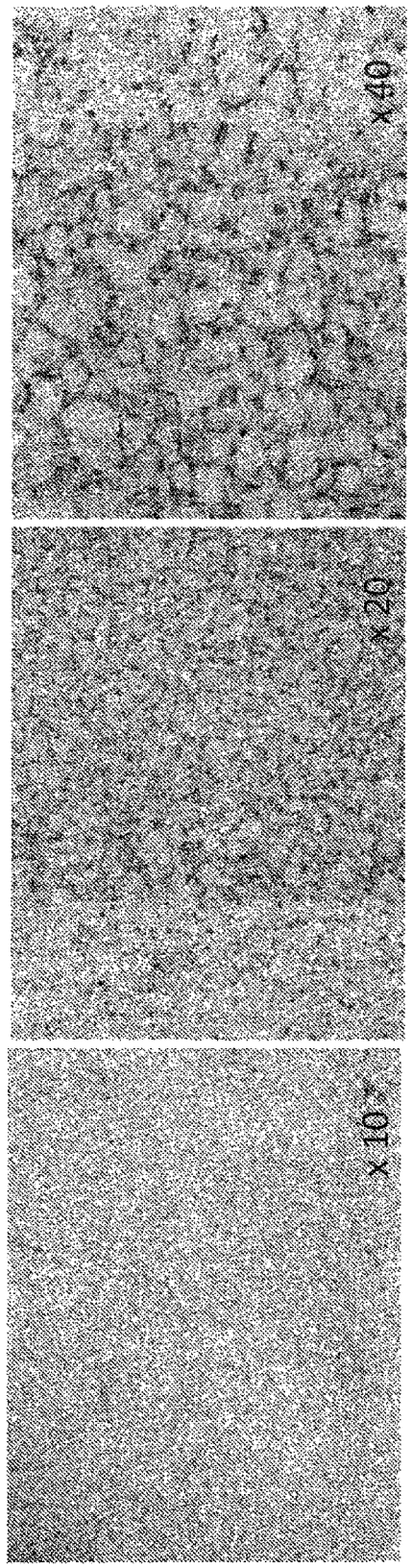
Figure 12:
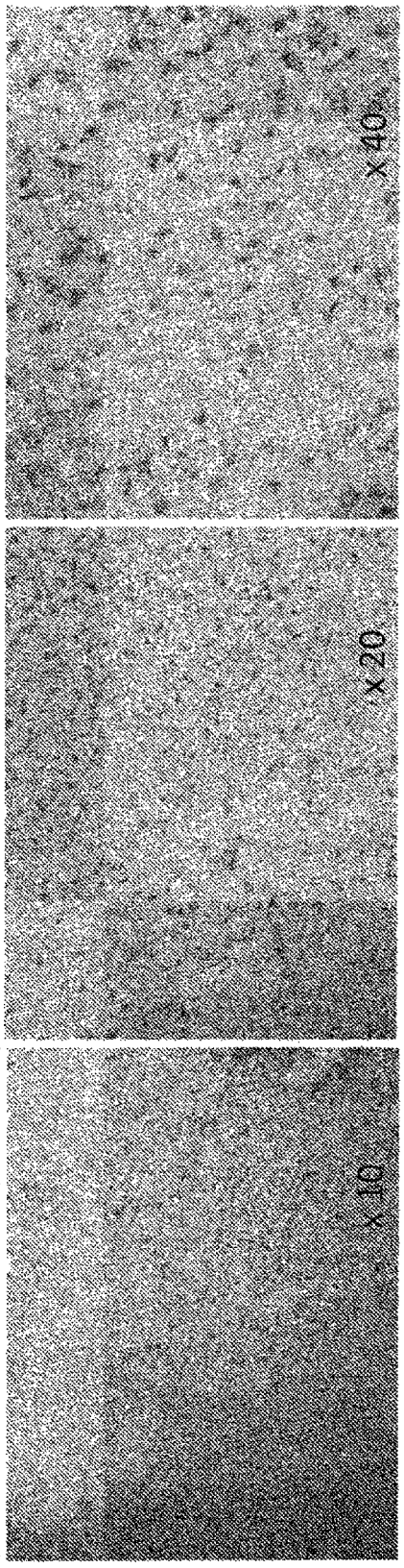

FIG. 12 shows the histological analysis of joints injected with BV$^{CAR}$ and HAdV5-PUMA control vectors, with respect to the duo vector BV$^{CAR}$HAdV5-PUMA. The freshly frozen sections (10 μm thick) of the heel joints of the three groups of rats receiving (a) BV$^{CAR}$ alone, (b) HAdV5-PUMA alone, or (c, d) the BV$^{CAR}$HAdV5-PUMA duo at different HAdV5-PUMA vector doses, 10$^7$ UFP (c) and 10$^9$ per joint (d), respectively, were stained with H&E and the presence of infiltrates in the synovial tissues was examined under an optical microscope. Photographs representing each group are presented with multiple enlargements: ×10, left-hand panel; ×20, central panel; and ×40, right-hand panel.

Figure 13:
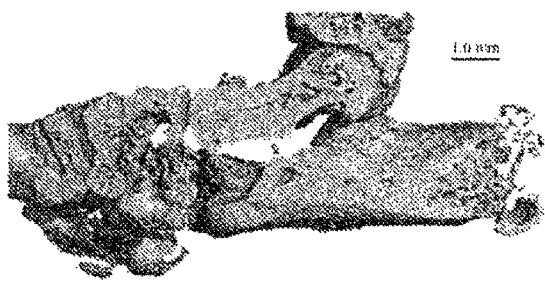
Figure 13:
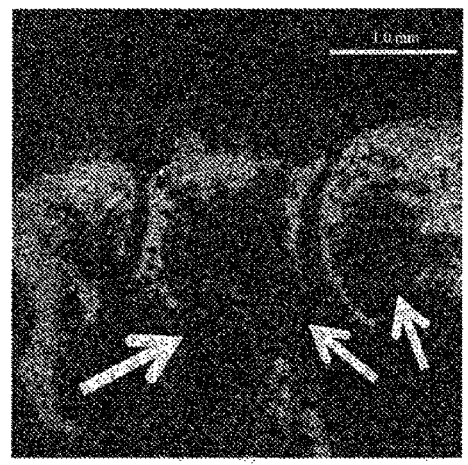
Figure 13:
Figure 13:
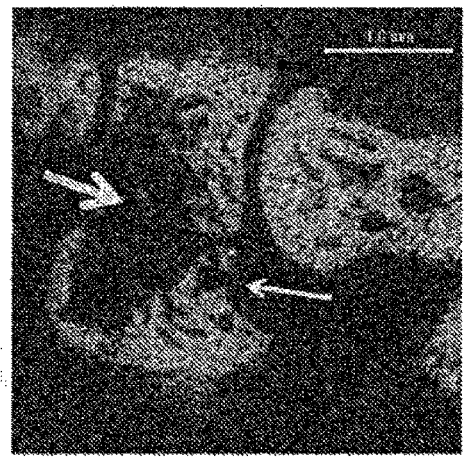
Figure 13:
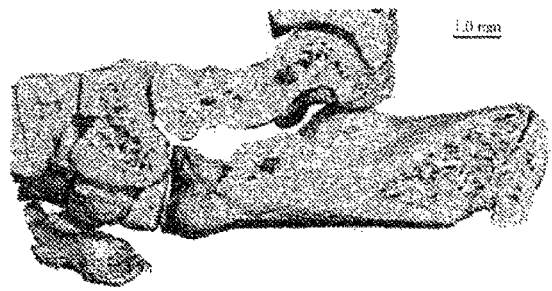
Figure 13:
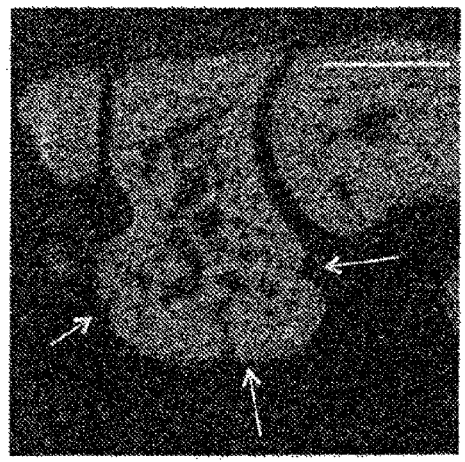
Figure 13:
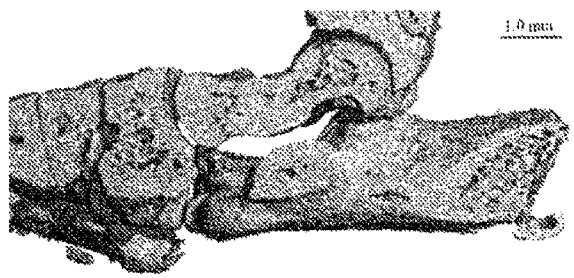
Figure 13:
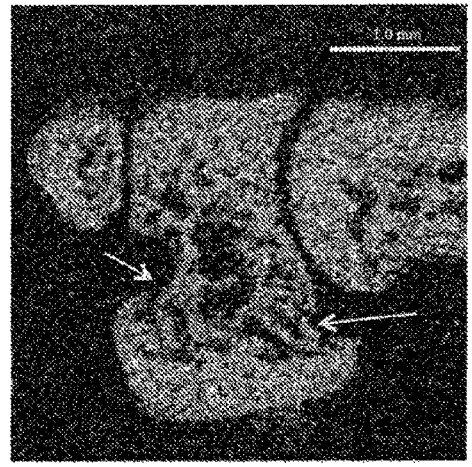
Figure 13:
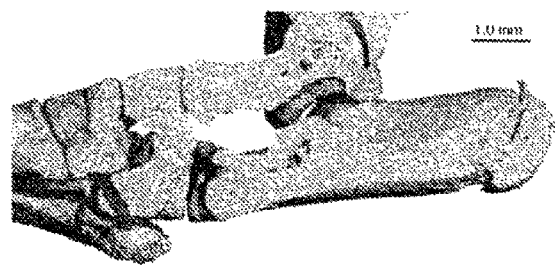
Figure 13:
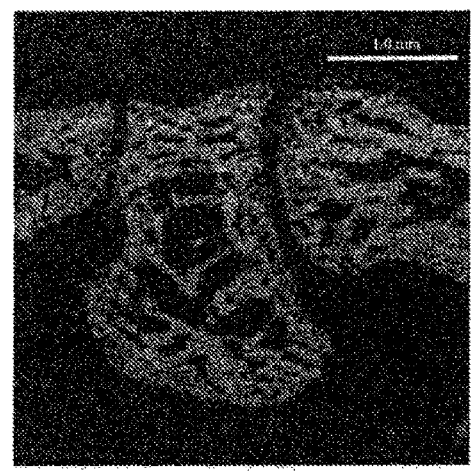

FIG. 13 shows the imaging of the heel tissues of rats by computerized micro-tomography (μ-CT). The rat heels were injected with (a) BV$^{CAR}$ alone, (b) HAdV5-PUMA alone, or (c, d) the BV$^{CAR}$HAdV5-PUMA duo at different HAdV5-PUMA vector doses, 10$^7$ UFP per joint (c) and 10$^9$ (d), respectively. (e), Negative control heel of a healthy rate of the same age. Left-hand panels, parasagittal sections of μ-CT showing, from left to right, the intermediate cuneiform, the navicular and the distal talus. The white arrows indicate bone erosion.

EXAMPLE 1

Transduction of Synoviocytes by HAdV5-BV$^{CAR}$

The synoviocytes used in the present examples were obtained from synovial tissue of patients with rheumatoid arthritis undergoing joint surgery and who satisfied the new criteria for rheumatoid arthritis established by the American College of Rheumatology (Aletaha et al., *Arthritis & Rheumatism*, 2569-81, 2010), and were then prepared as described in the PCT application WO 2011/042769.

Non-replicative HAdV5 vectors expressing the green fluorescent protein (GFP) under the control of the strong early-immediate promoter of the cytomegalovirus (CMV) were obtained as described in the PCT application WO 2011/042769 except that the human embryo kidney cells HEK-293 or "cells 293" (ATCC no. CRL-1573) were previously kept in monolayers in DMEM medium (Invitrogen) supplemented with 10% SVF (Invitrogen), penicillin (100 U/ml) and streptomycin (100 mg/ml) at 37° C. and 5% $CO_2$.

The recombinant baculovirus vector (BV) expressing the CAR protein (BV$^{CAR}$) was obtained as described in the PCT application WO 2011/042769.

The adenovirus and baculovirus vector complexes and the cells for the transduction tests were prepared as described in the PCT application WO 2011/042769.

The GFP cell expression was observed 36 hours after infection in fluorescence microscopy and quantified by flow cytometry. More specifically, the transduced cells were observed directly from the culture plate, by means of the Axiovert inverted microscope (Zeiss). The fluorescence images were taken with an Axiovert digital camera (Zeiss) and analyzed by means of the Axio Vision program (Zeiss). Then, for the flow cytometry analysis, the cells were fixed at the appropriate times with 2% paraformaldehyde in PBS for one night at 4° C., then rinsed once with PBS and analyzed for GFP fluorescence by means of a FACSCanto™ II cytometer and the DIVA 6 software (Becton Dickinson Biosciences).

Figure 1:
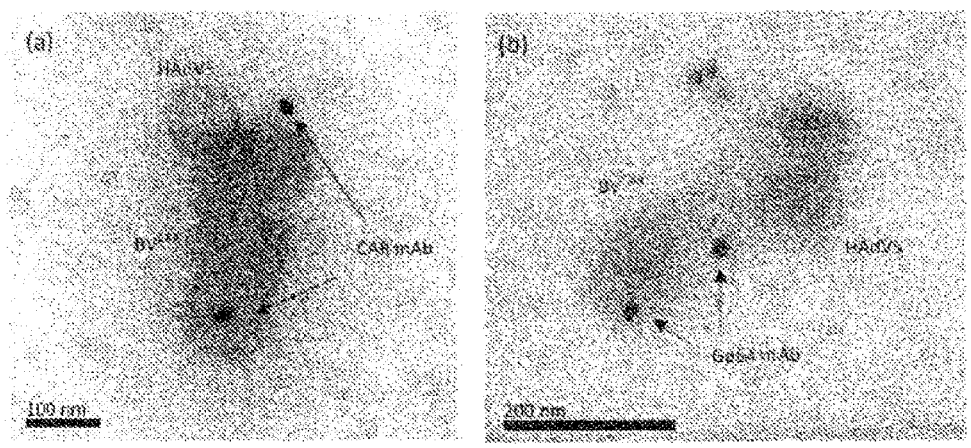

The HAdV5-BV$^{CAR}$ were observed by transmission electron microscopy with negatively stained samples labeled with antibodies coupled to gold particles ("immunogold" labeling). Monoclonal antibodies directed against the human CAR glycoprotein (clone E1.1, Hemmi et al., *Hum. Gene Ther.*, 9: 2363-2373, 1998) and against the gp64 baculovirus glycoprotein (clone AcV1, Santa Cruz Biotechnology, Inc.) were used to respectively label the presence of extrinsic CAR molecules on the BV$^{CAR}$ envelope (FIG. 1a) and the intrinsic gp64 envelope glycoprotein of the baculovirus (FIG. 1b).

Figure 2:
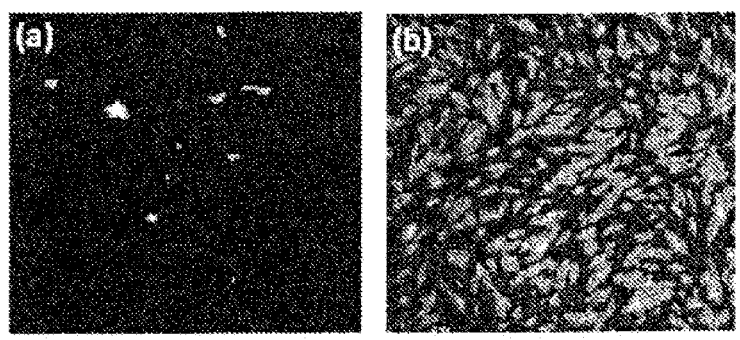
FIG. 2 shows the transduction of primary human synoviocytes, observed by fluorescence microscopy, by a HAdV5-GFP vector alone (FIG. 2a) or by a HAdV5-GFP-BV$^{CAR}$ complex (FIG. 2b).
Figure 3:
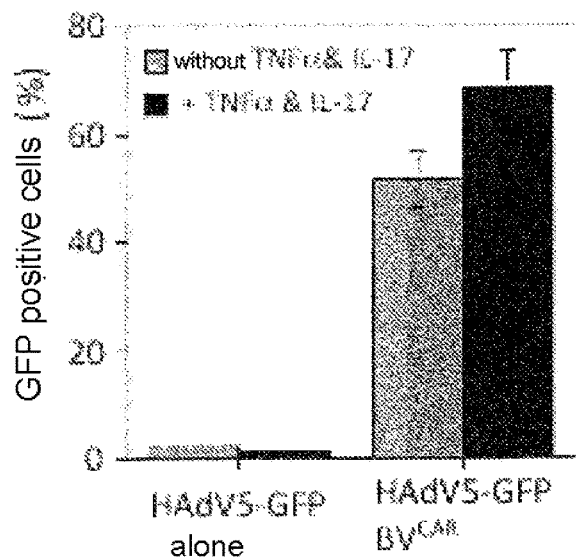
FIG. 3 shows the percentage of GFP positive cells, quantified by flow cytometry, in synoviocyte samples of FIGS. 2a and 2b, either not pretreated (without TNFα & IL-17), or pretreated with proinflammatory cytokines TNF-α and IL-17 (+TNFα & IL-17).

When the synoviocytes were infected with HAdV5-GFP alone at a vector dose of 20 viral particles per cell (vp/cell), the transduction efficacy is low, with less than 2% GFP positive cells (FIGS. 2a and 3). However, when the same HAdV5-GFP vector dose was complexed with BV$^{CAR}$, more than 50% GFP positive cells are observed (FIGS. 2b and 3). Surprisingly when the synoviocytes were pretreated with proinflammatory cytokines (TNF-α and IL-17) to mimic inflammatory conditions in the joints affected by arthritis, 70% of the cells infected with HAdV5-GFP-BV$^{CAR}$ were GFP positive (FIG. 3).

EXAMPLE 2

Expression of the PUMA Protein in Synoviocytes by Means of HAdV5-PUMA and Cell Death A vector based on HAdV5, carrying the PUMA gene under the control of the CMV promoter, and coupled to the recombinant BV$^{CAR}$ vector, was constructed, according to the protocol described in example 1, replacing GFP with PUMA, the PUMA gene thus being inserted in place of the E1 gene region itself deleted from the HAdV5 genome. The functionality of this HAdV5-GFP-BV$^{CAR}$ vector was evaluated in vitro in human primary synoviocytes.

Observation Under the Microscope

The cytological effects of the expression of the PUMA protein on the synoviocytes were first studied by comparing the synoviocytes infected by HAdV5-PUMA and the HAdV5-PUMA control vector. The two vectors were used at the same dose (50 vp/cell) and complexed with BV$^{CAR}$. The appearance of the cells in monolayer was observed 24 hours after infection with the microscope (FIG. 4). There was no change in the morphology of the mock-infected synoviocytes (FIG. 4a) or infected with HAdV5-GFP-BV$^{CAR}$ (FIG. 4b). The infection with HAdV5-PUMA-BV$^{CAR}$ showed massive cell death (FIG. 4c). These results confirm that the induction of cell death of synoviocytes is due to the PUMA protein.

To mimic the inflammatory conditions encountered in arthritic joints, the same experiment was performed on synoviocytes pre-treated with 3 different proinflammatory cytokines: TNF-α, IL-17 and IL-1β. Massive cell death occurred in the synoviocytes infected with HAdV5-PUMA-BV$^{CAR}$ (FIG. 4f), whereas no visible change could be observed in the mock-infected cells (FIG. 4d) and the cells infected with HAdV5-GFP-BV$^{CAR}$ (FIG. 4e).

Evaluation of the PUMA Expression Level

Three different isolates of human synoviocytes pretreated with TNF-α, IL-17 and IL-1β were infected or not (non-infected controls) by the HAdV5-PUMA-BV$^{CAR}$ complex in order to analyze the expression level of the PUMA protein. The cells were harvested after 24 hours of infection and the cell lysates were analyzed by polyacrylamide-SDS gel electrophoresis and immunotransfer (SDS-PAGE & Western blotting). To identify the PUMA protein, the following were used, in succession: (1) a polyclonal rabbit antibody directed against the human PUMA protein (obtained from the Epitomics firm), followed by (2) an anti-IgG rabbit antibody labeled with peroxidase (obtained from the Sigma firm); (3) the enzymatic reaction of the peroxidase was observed owing to a chemiluminescent substrate (West-Pico, sold by the Pierce firm). The non-infected control cells show a very low level of expression of the PUMA protein in human synoviocytes (so-called "basal" expression). However, in the cell samples infected by the HAdV5-PUMA-BV$^{CAR}$ complex, a significantly high level of expression of the PUMA protein, visible as a predominant band migrating to the expected position for a protein with a molecular mass of 18,000 daltons (18 kDa; FIG. 5).

Measurement of Cell Survival at Different Vector Doses

The results of the above microscope observation show that the use of HAdV5-PUMA-BV$^{CAR}$ at a dose of 50 vp/cell led to the death of almost all of the synoviocytes in monolayer, 24 hours after infection. The efficacy of the PUMA-induced cell death was determined for multiple vector doses, by living cell counts with the MTT test. For this, cells cultivated on 96-well flat-bottom plates were infected, and analyzed 36 hours after infection. The cell culture medium was then removed, and 30 μL of MTT solution (7.5 mg/ml of thiazolyl-tetrazolium bromide (Sigma-Aldrich) in PBS) were added to each well and incubated at 37° C. for 4 hours. The MTT solution was then removed and 100 μL of DMSO (dimethylsulfoxide, Sigma-Aldrich) were added to each well. The optical density of the supernatants in the 96-well plate was read at 570 nm.

The results are presented in FIG. 6 and are expressed as a percentage of cell survival with respect to the control. For the synoviocytes not treated with cytokines, the percentage of viable cells decreased as a function of the vector dose, with 90% viable cells with 5 vp/cell, 75% with 20 vp/cell, and 15% with 50 vp/cell. The synoviocytes infected by HAdV5-PUMA-BV$^{CAR}$ and treated with TNF-α showed a similar reduction in cell viability, with 83% cell survival with 5 vp/cell to around 10% with 50 vp/cell. Surprisingly, the synoviocytes pretreated with IL-17 or IL-β showed a significantly greater susceptibility to PUMA at low vector doses (5 to 20 vp/cell). The treatment of synoviocytes with TNF-α in combination with IL-17 or IL-β resulted in a greater sensitivity to PUMA-induced cell death, as observed with the treatments with IL-17 alone or IL-β alone. These results demonstrate that the level of PUMA-induced cell death is dependent upon the vector dose, and that the synoviocytes treated with proinflammatory cytokines are more sensitive to PUMA-induced cell death.

EXAMPLE 3

Cell Death Kinetics after Infection with HAdV5-PUMA-BV$^{Car}$

The PUMA-induced cell death kinetics of the synoviocytes treated or not by cytokines were determined by measuring the percentage of cell survival at times 0, 18, 24 and 48 hours after infection, using a constant dose of HAdV5-PUMA-BV$^{CAR}$ of 20 vp/cell, and analyzed by MTT test, as in example 2.

The basal cytotoxic effect caused by infection with a non-replicative HAdV5 vector was determined using HAdV5-GFP-BV$^{CAR}$ at the same vector dose as HAdV5-PUMA-BV$^{CAR}$. 18 hours after infection around 25% cell death was thus due to infection by HAdV5, independently of the effect of PUMA (FIG. 7A). Between 18 and 48 hours after infection, the percentage of viable cells remained stable, at around 70%. The infection with HAdV5-PUMA led to a rapid reduction in the proportion of viable cells, with 50% cell survival 18 hours after infection, and 30% 48 hours after infection.

The pretreatment of synoviocytes with TNF-α, IL-17 and the combination of the two cytokines increased the effect on cell death by the PUMA protein, by obtaining only 40% cell survival 18 hours after infection compared with 90% for the synoviocytes infected with the HAdV5-GFP-BV$^{CAR}$ control vector (FIGS. 7B to D). Between 18 and 48 hours, the percentage of cell survival remained stable at around 80% for the cells infected by the HAdV5-GFP-BV$^{CAR}$ control, while it gradually decreased to 30% for the cells infected by HAdV5-PUMA-BV$^{CAR}$. These results are consistent with the observations under microscope (FIG. 4) and confirm that PUMA is directly involved in the induction of rapid cell death of synoviocytes.

EXAMPLE 4

Nuclear Fragmentation and Apoptosis of Synoviocytes Infected by HAdV5-PUMA-BV$^{CAR}$ The fluorescence microscope observation of the synoviocytes incubated with the DAPI (4'-6'-diamidino-2-phenylindole) stain showed a fragmentation of the DNA in cells infected with HAdV5-PUMA-BV$^{CAR}$. A kinetic study indicated that this nuclear fragmentation occurred at 6 hours after infection, while the nuclei of the control cells, mock-infected, remained intact and whole (FIGS. 8a and b).

The induction of the DNA fragmentation and cell death by apoptosis in cells infected by HAdV5-PUMA-BV$^{CAR}$ was evaluated quantitatively 24 hours after infection, by quantification of nucleosomes by means of an ELISA kit (Cell Death Detection kit, Roche Diagnostics). For this, aliquots of synoviocytes ($10^5$ cells) were harvested 24 hours after infection, and centrifuged for minutes at 200 g. The cell pellets were then resuspended in 250 µl of incubation buffer and incubated for 30 minutes at room temperature. The cell lysates were centrifuged at 20,000 g for 10 minutes and the supernatants were used for apoptosis measurements. For this, one-tenth of each supernatant was incubated on a 96-well plate pre-coated with anti-histone antibodies (clone H11-4), labeled with biotin, for 90 minutes at room temperature. The wells were rinsed 3 times and 100 µl of solution containing an anti-DNA antibody (clone M-CA-33) conjugated with peroxidase were added to each well. The 96-well plate was then incubated again fro 90 minutes at room temperature. The wells were again rinsed 3 times before 100 µl of substrate solution (ABTS) was added to each well. Finally, the plate was incubated on a mixer (at 250 rpm) for around 20 minutes, and the optical density (OD) was measured at 405 nm.

This test immunochemically determined the DNA fragments complexed to the histones that were released in the cytoplasmic fraction of the lysates obtained from synoviocytes infected with HAdV5-PUMA-BV$^{CAR}$ at different vector doses. The lysates obtained from mock-infected cells served as negative controls and provided the basal level of nucleosomes physiologically released in the cytoplasm. In the absence of cytokines, the induction of apoptosis by PUMA was dose-dependent, with a release of cytoplasmic nucleosomes 6 times greater than the basal level, at the vector dose of 10 viral particles per cell (vp/cell), and 12 times greater at 20-40 vp/cell (FIG. 9). In the presence of TNF-α, IL-17, or these 2 cytokines (TNF-α, IL-17), the level of cytoplasmic nucleosomes increased significantly, to 12 to 15 times the basal level at the dose of 10 vp/cell, and remained at this plateau value for the highest doses.

EXAMPLE 5

Effect of HAdV5-PUMA-BV$^{CAR}$ on Synoviocytes Derived from Tissue Samples

Primary synoviocytes derived from 3 different patients were used to comparatively evaluate their sensitivity to PUMA-induced apoptosis. The infection with HAdV5-PUMA-BV$^{CAR}$ was performed at a vector dose of 30 vp/cell, in the absence or in the presence of proinflammatory cytokines, and the level of cytotoxicity was measured by the MTT test, as in example 2, over a period of 40 hours after infection. The cell survival curves of the three different clinical samples, shown in FIG. 10, show relatively similar profiles, with a rapid decrease in cell survival 16 hours after infection, followed by a more gradual decrease up to 40 hours. The infection with HAdV5-PUMA-BV$^{CAR}$ of the primary synoviocytes of patients 1 and 2 showed an effect on cell death that was significantly greater in the presence of cytokines, in particular IL-17, with respect to the effect observed in the absence of cytokines (FIGS. 10A and B). For the synoviocytes of patient 3, there was no difference in the induction of cell death between the cells treated or not treated with cytokines (FIG. 10C). In the three cases, the percentage of cell survival 40 hours after infection was drastically reduced, to 30% or less. These results demonstrate that the apoptosis induced by HAdV5-PUMA-BV$^{CAR}$ is effective and rapid for synoviocytes derived from different patients.

EXAMPLE 6

Effect of HAdV5-PUMA-BV$^{CAR}$ in an Animal Model of Arthritis

The therapeutic effect of HAdV5-PUMA-BV$^{CAR}$ was evaluated in the adjuvant-induced arthritis (AIA) model in the rat.

Experimental Protocol

Female Lewis rats of around 100 g (Laboratoires Janvier, Saint-Berthevin, France) received an injection of 300 µL (5 mg/mL) of lyophilized *Mycobacterium butyricum* (Difco Laboratories, Detroit, Mich., USA; Marotte et al., Rheumatology, 2010, 49, 467-479), subcutaneously, at the base of the tail. In this model, the first signs of joint inflammation and pain appear on D8 after the induction and reach a maximum at between D14 and D18 (Marotte et al., Rheumatology, 2010, 49, 467-479). Fourteen days (D14) after induction, various vectors were injected according to the following 6 groups (5 rats per group). The three control groups were recombinant baculovirus alone (BV$^{CAR}$; $10^5$ UFP per joint), the adenovirus vector carrying the PUMA gene alone (HAdV5-PUMA; $10^9$ UFP per joint), and BV$^{CAR}$ ($10^5$ UFP per joint) in combination with an empty adenoviral vector (HAdV5-null; $10^9$ UFP per joint). The three therapeutic groups consisted of the association of BV$^{CAR}$ ($10^5$ UFP per joint) with HAdV5-PUMA at 3 concentrations ($10^7$, $10^8$, and $10^9$ UFP per joint, respectively). The clinical parameters were evaluated every day after the intra-articular injection, for 4 days, and included a joint index, the heel circumference and the body mass. All of the animals were euthanized at D4 after the intra-articular injection. The scores of the joint indices were recorded for each posterior joint, in a blind manner, by a consistent observer, then the averages were calculated for each animal. The scores were expressed on a scale of 0 to 4, on which 0=no swelling or erythema, 1=slight swelling and/or erythema, 2=mild to moderate edema, 3=marked edema with limited use of the joint, and 4=excessive edema with rigidity of the joint. The heel circumferences were measured, in a blind manner, by the same observer, as described above (Marotte et al., Rheumatology, 2010, 49, 467-479). The right heels of the euthanized animals were cut up, sampled, placed in Neg50 (Thermo Scientific Waltham, Mass.), then frozen in liquid nitrogen. The frozen right heels were scanned by micro-computerized tomography (µ-CT; viva-CT40, Scanco, Brütisellen, Switzerland). The three-dimensional reconstructions were segmented using the following parameters: sigma, 2.8; support, 2; threshold, 289.

After the microtomography acquisition, the sections of the freshly frozen joints (10 μm in thickness) of the different groups were stained with hematoxylin and eosin, and the presence of infiltrates was examined.

Reduction in Joint Inflammation by Intra-Articular Injection of BV$^{CAR}$HAdV5-PUMA in an AIA Model in the Rat In view of the encouraging results obtained in vitro and ex vivo, the effect of BV$^{CAR}$HAdV5-PUMA in vivo was then explored. In the AIA inflammatory arthritis model, the rats develop arthritis 8-10 days after injection of adjuvant. After the appearance of arthritis, i.e. on day 14 (D14) post-induction, the vectors were administered by intra-articular injection into the heel. Thirty rats divided into 6 groups (5 rats per group) were used. The three control groups consisted of: (i) of BV$^{CAR}$ alone ($10^5$ UFP per joint), (ii) HAdV5-PUMA alone ($10^9$ UFP per joint), and (iii) BV$^{CAR}$-HAdV5-null ($10^5$ UFP BV$^{CAR}$+$10^9$ UFP HAdV5-null per joint) complex. The three therapeutic groups consisted of BV$^{CAR}$ ($10^5$ UFP per joint) complexed with HAdV5-PUMA at 3 different doses ($10^7$, $10^8$, $10^9$ UFP per joint, respectively).

The administration of BV$^{CAR}$ or HAdV5-PUMA control vectors alone, or of the BV$^{CAR}$HAdV5-null control complex, did not produce any detectable beneficial effect on the change in the arthritis (FIG. 11). However, BV$^{CAR}$HAdV5-PUMA significantly improved the parameters of all of the rats. BV$^{CAR}$HAdV5-PUMA showed a strong reduction in the variation in heel circumference and this effect occurred in a dose-dependent manner (FIG. 11A). Similarly, BV$^{CAR}$-HAdV5-PUMA induced a dose-dependent decrease in the joint index score, but the difference with the control vectors for this parameter were significant at the highest doses of the vector ($10^9$ UFP per joint; FIG. 11B). In addition, the body masses of the rats injected with BV$^{CAR}$HAdV5-PUMA were superior to those of the control animals for all doses of BV$^{CAR}$HAdV5-PUMA tested (FIG. 11C).

Histological Analysis of Rat Heels

The efficacy of the treatment was studied both on joint and bone tissue. The alterations in the synovium were evaluated by optical microscopy on freshly frozen joint sections, after standard staining with hematoxylin and eosin (FIG. 12). The infiltrates were significantly reduced in the joints treated with BV$^{CAR}$HAdV5-PUMA, by comparison with the joints treated with BV$^{CAR}$ alone (FIG. 12b) or HAdV5-PUMA alone (FIG. 12b). This effect is dose-dependent with a less pronounced decrease in the number of infiltrates at $10^7$ UFP (FIG. 8c) than at $10^9$ UFP of BV$^{CAR}$HAdV5-PUMA per heel joint (FIG. 8d).

Imaging of Rat Heel Tissue by High-Resolution X-Ray Micro-Computerized Tomography (μ-CT)

The bone tissue alterations in the rats were studied ex vivo using μ-CT. Three-dimensional images enabled a complete evaluation of bone loss in the joints, while the finer details were detected on the parasagittal sections. Significant tissue alterations were observed in the joints of rats injected with BV$^{CAR}$ alone (FIG. 13a). Extended bone loss was visible in the joints of rats injected with HAdV5-PUMA alone (FIG. 13b). By contrast, in the joints injected with BV$^{CAR}$HAdV5-PUMA complexes, only discrete morphological changes were observed (FIGS. 13c, 13d), with respect to the heel joints of healthy rats (FIG. 13e). The only bone loss marker perceptible in the joints treated with BV$^{CAR}$HAdV5-PUMA were changes in porosity, characteristics of the early phase of arthritis. Additional changes in microarchitecture, following extended inflammation, were not observed in the joints treated with BV$^{CAR}$HAdV5-PUMA.

CONCLUSIONS

The net effect of the duo BV$^{CAR}$HAdV5-PUMA vector on the control of synoviocyte proliferation observed in vitro and ex vivo led the inventors to study the effects of the expression of the pro-apoptotic PUMA gene in vivo. To do this, the inventors used BV$^{CAR}$HAdV5-PUMA in the AIA model in the rat, an animal model widely recognized and consistent with rheumatoid arthritis in humans.

The results observed in the heels of rats injected with BV$^{CAR}$HAdV5-PUMA, compared with the control vectors, confirm those obtained in vitro and ex vivo. All of the beneficial effects of the BV$^{CAR}$HAdV5-PUMA duo vector occurred in a dose-dependent manner, and include (i) a significant increase in the functionality of the joint, (ii) a significant decrease in local inflammation, and (iii) an absence or a minimal degree of alterations of the joint and bone loss, detectable by histopathology and μ-CT. By comparison, the administration of BV$^{CAR}$ or HAdV5-PUMA control vectors alone, or of the BV$^{CAR}$HAdV5-null control complex, did not produce any detectable beneficial effect on the change in the arthritis.

Unlike the conventional vectors derived from HAdV5, which have a pro-inflammatory activity, BV$^{CAR}$HAdV5-PUMA has a global joint anti-inflammatory action. This joint anti-inflammatory action is significant by comparison with the discrete reduction observed with the HAdV5-PUMA vector. Moreover, the significant joint anti-inflammatory activity of BV$^{CAR}$HAdV5-PUMA is detected at doses 10 times lower (in terms of viral particles of the active HAdV5-PUMA vector) than those used with the HAdV5-PUMA vector.

All of these results demonstrate the therapeutic potential of the BV$^{CAR}$HAdV5-PUMA complex in the local treatment of joint pathologies.

The invention claimed is:

1. A method of local treatment of a joint disease in a subject, comprising administering to the subject a complex consisting of
   (a) a recombinant adenovirus expressing the gene coding for the p53 up-regulated modulator of apoptosis (PUMA) protein under the control of a functional promoter in a mammal cell, and
   (b) a recombinant baculovirus containing a mammal coxsackie-adenovirus receptor (CAR) inserted into its envelope in an amount sufficient to induce apoptosis of synoviocytes in the subject, wherein the apoptosis of the synoviocytes in the subject causes a functional and anatomical improvement in a treated joint.

2. The method of claim 1, wherein said joint disease is an inflammatory disease.

3. The method of claim 1, wherein said joint disease is selected from group consisting of rheumatoid arthritis, inflammatory rheumatism, arthritis flare-ups, chondrocalcinosis, gout, hemophilic arthropathy, loosening of prosthetic joints, and synovial tumors.

4. The method of claim 1, wherein the PUMA protein is a human PUMA protein.

5. The method of claim 1, wherein the adenovirus is the human adenovirus of serotype 5 (HAdV5).

6. The method of claim 1, wherein the baculovirus is a virus of the nuclear polyhedrosis group I chosen from the multiple nuclear polyhedrosis virus *Autographa californica* (AcMNPV) and the nuclear polyhedrosis virus *Bombyx mori* (BmNPV).

7. The method of claim 1, wherein the CAR receptor is a mammalian CAR receptor.

8. The method of claim 7, wherein the mammalian CAR receptor is a human CAR receptor.

\* \* \* \* \*